(12) United States Patent
Araki et al.

(10) Patent No.: US 6,839,130 B2
(45) Date of Patent: Jan. 4, 2005

(54) OPTICAL FIBER MEASURING APPARATUS

(75) Inventors: Tetsuya Araki, Kumamoto (JP); Katsumi Hirata, Tokyo (JP)

(73) Assignees: Ando Electric Co., Ltd., Tokyo (JP); Kyusyu Ando Electric Co., Ltd., Kumamoto (JP)

( * ) Notice: Subject to any disclaimer, the term of this patent is extended or adjusted under 35 U.S.C. 154(b) by 334 days.

(21) Appl. No.: 10/211,760

(22) Filed: Aug. 2, 2002

(65) Prior Publication Data

US 2003/0025900 A1 Feb. 6, 2003

(30) Foreign Application Priority Data

Aug. 3, 2001 (JP) ........................................ 2001-236922

(51) Int. Cl.$^7$ .............................................. G01N 21/00
(52) U.S. Cl. ..................................................... 356/73.1
(58) Field of Search ..................... 356/73.1; 398/9–38, 398/154–161; 385/24, 3, 12–16, 37, 40; 250/227.11, 227.17, 227.15

(56) References Cited

U.S. PATENT DOCUMENTS

| | | | | |
|---|---|---|---|---|
| 4,893,006 A | * | 1/1990 | Wakai et al. | 356/73.1 |
| 5,129,721 A | * | 7/1992 | Sakamoto et al. | 356/73.1 |
| 5,453,826 A | * | 9/1995 | Sugimoto et al. | 356/73.1 |
| 5,557,401 A | * | 9/1996 | Maeda et al. | 356/73.1 |

* cited by examiner

*Primary Examiner*—Tu T. Nguyen
(74) *Attorney, Agent, or Firm*—Fish & Richardson P.C.

(57) ABSTRACT

An optical pulse $\lambda 0$ from a light source section 10 is incident upon an optical fiber 1 through an optical demultiplexer section 20, and its return light is supplied to an optical/electrical processing section 30 as the light of a plurality of different wavelengths $\lambda 1$ to $\lambda n$ by the optical demultiplexer section 20, and is respectively converted into electrical signals. Signals of the converted return light are respectively sampled and are averaged by respective processing circuits 402 to 40$n$ of a signal processing section 40 so as to be formed as desired measurement waveforms. In the measurement waveforms, which are the results, data for corresponding sampling points are expressed as measurement data at an identical distance in the optical fiber.

5 Claims, 5 Drawing Sheets

OPTICAL FIBER MEASURING APPARATUS

FIELD OF THE INVENTION

The present invention relates to an optical fiber measuring apparatus, and more particularly to an optical fiber measuring apparatus suitable for use in the measurement of characteristics of an optical fiber used in, for example, optical communication.

BACKGROUND OF THE INVENTION

As a measuring apparatus for detecting the transmission loss characteristic of an optical fiber or its connected portion for detecting a deteriorated portion such as a fractured point, an optical fiber measuring apparatus is known which uses a so-called optical time-domain reflector (OTDR) in which measurement is effected by detecting its backscattered light and reflected light.

Conventionally, the optical fiber measuring apparatus such as the one described above includes an optical pulse generating source for generating predetermined optical pulses which are made incident upon an optical fiber subject to measurement. The optical pulse generating source is a light source such as a laser for generating optical pulses of a predetermined wavelength and is repeatedly driven at predetermined timings to generate optical pulses at predetermined intervals. The optical pulses which are repeatedly generated from the light source are made incident from one end of the optical fiber subject to measurement through an optical pulse input/output circuit such as an optical directional coupler. The return light is detected by a light receiver such as a photodiode through the optical directional coupler. The detected return light is converted into an electrical signal and outputted by the photodiode, is amplified by an amplifier, and is supplied to a signal processing circuit. The signal processing circuit effects sampling with respect to the signal of the return light, which is converted into the electrical signal and amplified, at predetermined timings corresponding to the repetition timing at the optical pulse generating source. The sampled signals are averaged in correspondence with the number of repetition of the optical pulses, and a loss characteristic corresponding to that signal level is determined. Further, the results of processing are subjected to, for example, logarithmic conversion, and a rightwardly descending loss waveform is formed, the waveform being displayed on a display section.

However, with the above-described conventional technique, when the return light of a plurality of different wavelengths scattered or reflected in the optical fiber is measured, the return light of a wavelength to be measured is detected by effecting a changeover in an optical pulse input/output circuit, and measurement must be effected for each wavelength. Therefore, there have been problems in that it takes time in measuring all the return light of the plurality of wavelengths to be measured, and time and trouble are involved in its changeover operation. Accordingly, an arrangement is conceivable in which the return light is outputted by being divided into a plurality of wavelengths through a filter or the like, the respective return light is detected by a plurality of detecting circuits, and signal processing is effected at a time by a plurality of signal processing circuits. In this case, however, since the speed of light advancing in the optical fiber differs depending on the wavelength, in the case of the return light of different wavelengths detected simultaneously, signals in which the reflected position in the optical fiber, i.e., the distance from a detecting end, differs are detected and processed. Therefore, there arises the problem that accurate comparison of data obtained from those results becomes difficult in some cases.

SUMMARY OF THE INVENTION

The invention is devised in view of the above-described circumstances, and its object is to provide an optical fiber measuring apparatus which makes it possible to detect the return light of a plurality of different wavelengths speedily and accurately and effect relative measurement thereof.

To solve the above-described problems, in accordance with the invention there is provided an optical fiber measuring apparatus in which predetermined optical pulses are incident from one end of an optical fiber 1 subject to measurement, and signal levels of return light thereof are detected to measure characteristics of the optical fiber, characterized by comprising: optical-pulse generating section 10 for generating predetermined optical pulses incident upon the optical fiber 1 subject to measurement; optical-pulse input/output section 20 to which the one end of the optical fiber subject to measurement is connected and which makes the optical pulses from the optical-pulse generating section incident upon the optical fiber and detects return light thereof, the optical-pulse input/output section being adapted to demultiplex the return light of the plurality of wavelengths scattered or reflected inside the optical fiber and output the same; a plurality of optical/electrical processing section 30 for converting the light of the respective wavelengths from the optical-pulse input/output section into electrical signals and for amplifying the electrical signals; a plurality of signal processing section 40 for sampling the signals of the respective wavelengths from the optical/electrical processing section and for effecting addition processing with respect to the sampled signals, so as to form waveforms expressing characteristics of the respective wavelengths; a plurality of clock generating section 50 for generating sampling clocks corresponding to speeds of the return light of the respective wavelengths and supplying the sampling clocks to the signal processing section; and timing control section 60 for supplying a first timing signal T1 representing an optical-pulse generating timing to the optical-pulse generating section 10, and for supplying a second timing signal T2 representing an addition processing timing to each of the signal processing section 40, the timing control section being adapted to generate the respective timing signals on the basis of a phase difference of the sampling clocks generated by the clock generating section 50.

In this case, each of the signal processing section 40 may include A/D converting section 412 for effecting analog-to-digital conversion of the signal of return light from the optical/electrical processing section 30 on the basis of the sampling clocks supplied by the clock generating section 50 and for sampling the signal, and addition processing section 414 for effecting addition processing with respect to the signal from the A/D converting section on the basis of the second timing signal T2 from the timing control section 60, wherein sampling frequencies of the clock generating section 50 may be set such that sampling resolutions of the sampling clocks to the A/D converting section 412 assume similar values with respect to the signals of the respective wavelengths, and the timing control section 60 may generate the second timing signal to the addition processing section 414 in a case where the phase difference of the sampling clocks from the clock generating section 50 falls within a predetermined range.

Advantageously, the timing control section 60 may include phase comparing section 604 for comparing the phases of the sampling clocks generated by the clock generating section 50, start-signal generating section 602 for generating start signals when the first and the second timing signals are generated on the basis of the result of comparison by the phase comparing section and a measurement start signal at the time of starting measurement, and timing-signal generating section 606 for starting the generation of the first and the second timing signals on the basis of the start signals from the start-signal generating section.

In addition, each of the signal processing section 40 may include A/D converting section 412 for effecting analog-to-digital conversion of the signal of the return light from the optical/electrical processing section 30 on the basis of the sampling clocks supplied by the clock generating section 50 and for sampling the signal, and addition processing section 414 for effecting addition processing with respect to the signal from the A/D converting section on the basis of the second timing signal T2 from the timing control section 60, wherein the clock generating section 50 may supply the sampling clocks to the A/D converting section 412 with respect to the signals of the respective wavelengths through delay section 804 to 80n capable of changing an amount of delay, and the amount of delay of the delay section may be calculated on the basis of the phase difference of the sampling clocks generated by the clock generating section 50.

In this case, the timing control section 60 may include phase comparing section 604 for comparing the phases of the sampling clocks generated by the clock generating section 50, start-signal generating section 602 for generating a start signal when the timing signal is generated upon receipt of a measurement start signal at the time of starting measurement, timing-signal generating section 606 for generating the timing signal on the basis of the start signal generated by the start-signal generating section and one of the clocks generated by the clock generating section, and delay control section 608 for controlling the amount of delay of the delay section on the basis of the timing signal from the timing-signal generating section and a result of comparison by the phase comparing section.

DETAILED DESCRIPTION OF THE PREFERRED EMBODIMENTS

Figure 1:
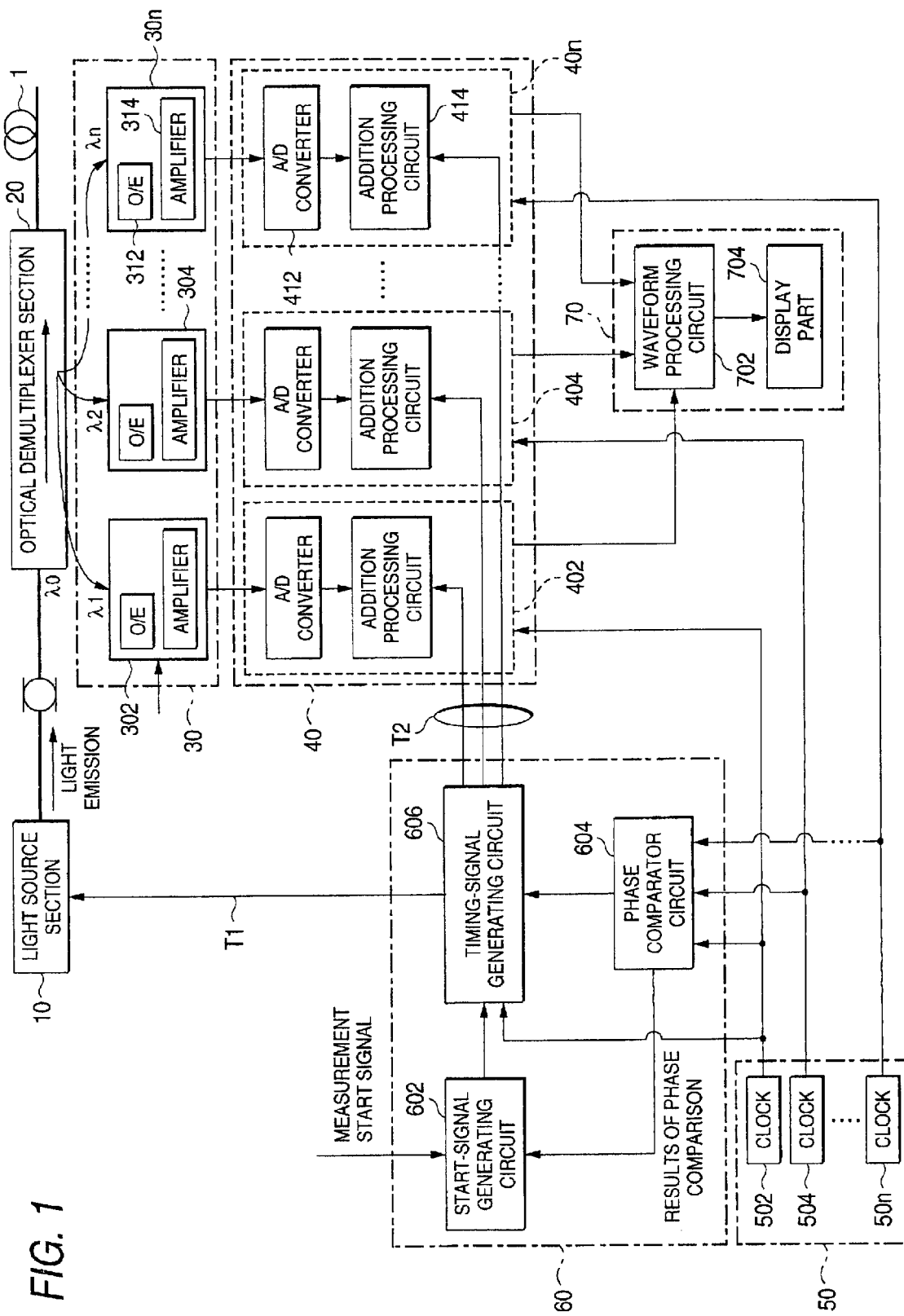
FIG. 1 is a functional block diagram illustrating an embodiment of an optical fiber measuring apparatus in accordance with the invention.

Referring now to the appended drawings, a detailed description will be given of the embodiments of the optical fiber measuring apparatus in accordance with the invention. FIG. 1 shows an embodiment of the optical fiber measuring apparatus in accordance with the invention. The optical fiber measuring apparatus in accordance with this embodiment is a measuring apparatus whereby the return light of optical pulses with a predetermined wavelength $\lambda 0$ incident from one end of an optical fiber 1 subject to measurement is detected at the one end to measure the characteristics of the optical fiber 1 representing the waveform of its loss and the like. In this embodiment, the optical fiber measuring apparatus in accordance with this embodiment is a multiple wavelength-compatible optical fiber measuring apparatus for detecting and measuring at a time the return light $\lambda 1$ to $\lambda n$ with a plurality of different wavelengths backscattered or reflected inside the optical fiber 1. In particular, major features of this embodiment lie in that the optical fiber measuring apparatus comprise a plurality of clock generators 502 to 50n for generating sampling clocks of frequencies corresponding to the wavelengths of the respective return light $\lambda 1$ to $\lambda n$, as well as a timing control section 60 for controlling the timings for effecting addition processing on the basis of the phase difference of the sampling clocks generated when the signals of the return light of the respective wavelengths are sampled and the sampled signals of the return light are averaged.

More specifically, as shown in FIG. 1, the optical fiber measuring apparatus in accordance with this embodiment includes a light source section 10, an optical demultiplexer section 20, an optical/electrical processing section 30, a signal processing section 40, a clock generating section 50, the timing control section 60, and a display processing section 70. The light source section 10 is an optical pulse generating circuit including a laser for generating optical pulses of a predetermined wavelength $\lambda 0$ and a drive circuit for driving the same. In this embodiment, the light source section 10 is a circuit for repeatedly generating the optical pulses in response to a first timing signal T1 from the timing control section 60. The optical pulses from the light source 10 are supplied to the optical fiber 1 through the optical demultiplexer section 20.

The optical demultiplexer section 20 is an optical pulse input/output circuit for detecting the return light from one end of the optical fiber 1 subject to measurement when optical pulses from the light source section 10 are incident from the one end of the optical fiber 1. In this embodiment, the optical demultiplexer section 20 includes, for instance, an optical directional coupler for inputting and outputting optical pulses to and from the optical fiber, as well as a spectral filter for demultiplexing the return light into a plurality of wavelengths $\lambda 1$ to $\lambda n$ and for outputting the same. The return light of the wavelengths $\lambda 1$ to $\lambda n$ detected by the optical demultiplexer section 20 is respectively supplied to the optical/electrical processing section 30.

The optical/electrical processing section 30 is a circuit for converting the return light from the optical demultiplexer section 20 into an electrical signal and amplifying it to a predetermined value. In this embodiment, the optical/electrical processing section 30 is comprised of first to n-th processing circuits 302 to 30n each including a light receiver (O/E) 312, such as a photodiode, for converting the detected light into an electrical signal and an amplifier (AMP) 314 for amplifying an electrical signal which is its output. The signal of the return light converted into the electrical signal and amplified is supplied to the signal processing section 40.

The signal processing section 40 is a processing circuit for determining signal waveforms which are expressed by the respective signals of the return light. In this embodiment, the signal processing section 40 is comprised of first to n-th processing circuits 402 to 40n each including an A/D converter 412 and an addition processing circuit 414. The A/D converter 412 is a conversion circuit for effecting analog-to-digital conversion of the respective signals of the return light from the optical/electrical processing section 30. In this embodiment, the A/D converter 412 receives from the clock generating section 50 sampling clocks of frequencies corresponding to the wavelengths of the respective return light λ1 to λn, and samples the signals, respectively. The addition processing circuit 414 is an arithmetic circuit for outputting an arithmetic mean of the digital signals of the return light converted by the A/D converter 412. In this embodiment, the addition processing circuit 414 effects arithmetic processing in response to a second timing signal T2 from the timing control section 60. The results of the operation are consecutively supplied to the display processing section 70.

The clock generating section 50 is a generator circuit for generating predetermined sampling clocks when sampling is effected by the aforementioned signal processing section 40. In this embodiment, the clock generating section 50 includes the first to n-th generators 502 to 50n for generating sampling clocks of respective frequencies corresponding to the wavelengths λ1 to λn of the return light. The sampling clocks from these first to n-th generators 502 to 50n are supplied to the corresponding processing circuits 402 to 40n.

Meanwhile, the timing control section 60 is a control circuit for supplying predetermined timing signals to the light source section 10 and the signal processing section 40 and for controlling the timings. In this embodiment, the timing control section 60 includes a start-signal generating circuit 602, a phase comparator circuit 604, and a timing-signal generating circuit 606, as shown in the drawing. The start-signal generating circuit 602 is a signal generating circuit, when an unillustrated start button is pressed, detects the same and generates a start signal at the time of generating a timing signal. In this embodiment, the start-signal generating circuit 602 generates the start signal on the basis of the result of comparison from the phase comparator circuit 604 on the pressing of the start button. The generated start signal is supplied to the timing-signal generating circuit 606.

The phase comparator circuit 604 is a circuit which compares the phase difference between the sampling clocks from the respective generators 502 to 50n of the clock generating section 50, and outputs the results. In this embodiment, the phase comparator circuit 604 supplies the result to the start-signal generating circuit 602 in a case where the phase difference falls within a predetermined range. The timing-signal generating circuit 606 is a signal generating circuit for generating the first timing signal T1 for the light source section 10 and the second timing signals T2 for the signal processing section 40, respectively. In this embodiment, the timing-signal generating circuit 606 starts the generation of the respective timing signals T1 and T2 upon receiving the start signal from the start-signal generating circuit 602. The generated first timing signal T1 is supplied to the light source section 10 at a predetermined interval, while the second timing signals T2 are supplied to the respective addition processing circuits 402 to 40n of the signal processing section 40 at intervals based on the sampling clock from, for instance, the first generator 502.

On the other hand, the display processing section 70 is a processing circuit which effects the display processing of the results of signal processing of the return light from the signal processing section 40 as a signal waveform of a predetermined format. In this embodiment, the display processing section 70 includes a waveform processing circuit 702 and a display part 704. The waveform processing circuit 702 includes, for example, a logarithmic conversion circuit for subjecting the signal level of the waveform formed by being averaged to logarithmic conversion, and a storage circuit for storing the results. In this embodiment, the results of logarithmic conversion are stored in the storage circuit as a substantially rightwardly descending waveform in proportion to the loss characteristic of the optical fiber 1, and are supplied to the display part 704 together with data on the respective wavelengths. The display part 704 includes a display section such as a cathode ray tube (CRT), and the display part 704 is more advantageous if it includes a circuit for printing the displayed measured waveform in the form of a hard copy or the like.

A description will be given of the operation of the optical fiber measuring apparatus in accordance with this embodiment having the above-described configuration. First, the power source is turned on, and the wavelengths λ1 to λn to be measured are respectively set. As a result, the desired generators 502 to 50n corresponding to the set wavelengths of the clock generating section 50 are respectively started to generate sampling clocks of frequencies corresponding to the respective wavelengths. The generated sampling clocks are respectively supplied to the respective processing circuits 402 to 40n of the signal processing section 40 and the phase comparator circuit 604 of the timing control section 60.

Next, upon receiving the sampling clocks from the clock generating section 50, the phase comparator circuit 604 compares the phase difference of the sampling clocks, and determines whether or not the result of comparison falls within a predetermined range. When the phase difference of the clocks falls within the predetermined range, the results are consecutively supplied to the start-signal generating circuit 602. When the start button is pressed in this state, the pressing of the start button is detected by the start-signal generating circuit 602 of the timing control section 60, and in a case where the result of comparison by the phase comparator circuit 604 falls within a predetermined range, the start signal is supplied from the start-signal generating circuit 602 to the timing generating circuit 606.

Next, upon receiving the start signal, the timing-signal generating circuit 606 first generates the first timing signal T1 at predetermined intervals and supplies them consecutively to the light source section 10. Consequently, the light source section 10, upon receiving the first timing signal T1 through its drive circuit, supplies a drive signal to the laser in response to that timing signal T1. As a result, optical pulses of a predetermined wavelength λ0 are repeatedly generated at predetermined intervals from the laser.

Next, the optical pulse of the predetermined wavelength from the light source section 10 is made incident from one end of the optical fiber 1 through the optical demultiplexer section 20, and part of it is backscattered due to such as the nonuniform distribution of the refraction index of the core or reflected at such as a connected portion or a deteriorated portion, and returns to the incident end as the light of the plurality of different wavelengths λ1 to λn. The light which returned to the incident end is respectively demultiplexed into the return light of the wavelengths λ1 to λn through the optical demultiplexer section 20, and is supplied to the respective processing circuits 302 to 30n of the optical/electrical processing section 30. Next, each of the processing circuits 302 to 30n of the optical/electrical processing section 30 converts the return light received by its light receiver 312 into an electrical signal corresponding to the intensity of the detected light and outputs the same. The resultant signal is amplified by the amplifier 314, and is supplied to a corresponding one of the processing circuits 402 to 40n of the signal processing section 40.

Next, in the signal processing section 40, the detected signals from the amplifiers are respectively subjected to sampling by the A/D converters 412 in response to the sampling clocks from the clock generating section 50, and the results are supplied to the addition processing circuits 414. At that time, the timing-signal generating circuit 606 of the timing control section 60 generates the second timing signals T2, and supplies them to the addition processing circuits 414 in the respective processing circuits 402 to 40n of the signal processing section 40. Consequently, the addition processing circuit 414 which received the signals of the sampled return light averages them, and generates data on the loss characteristic corresponding to the distance of the optical fiber 1 from a predetermined waveform corresponding to the intensity of the return light.

Figure 2:
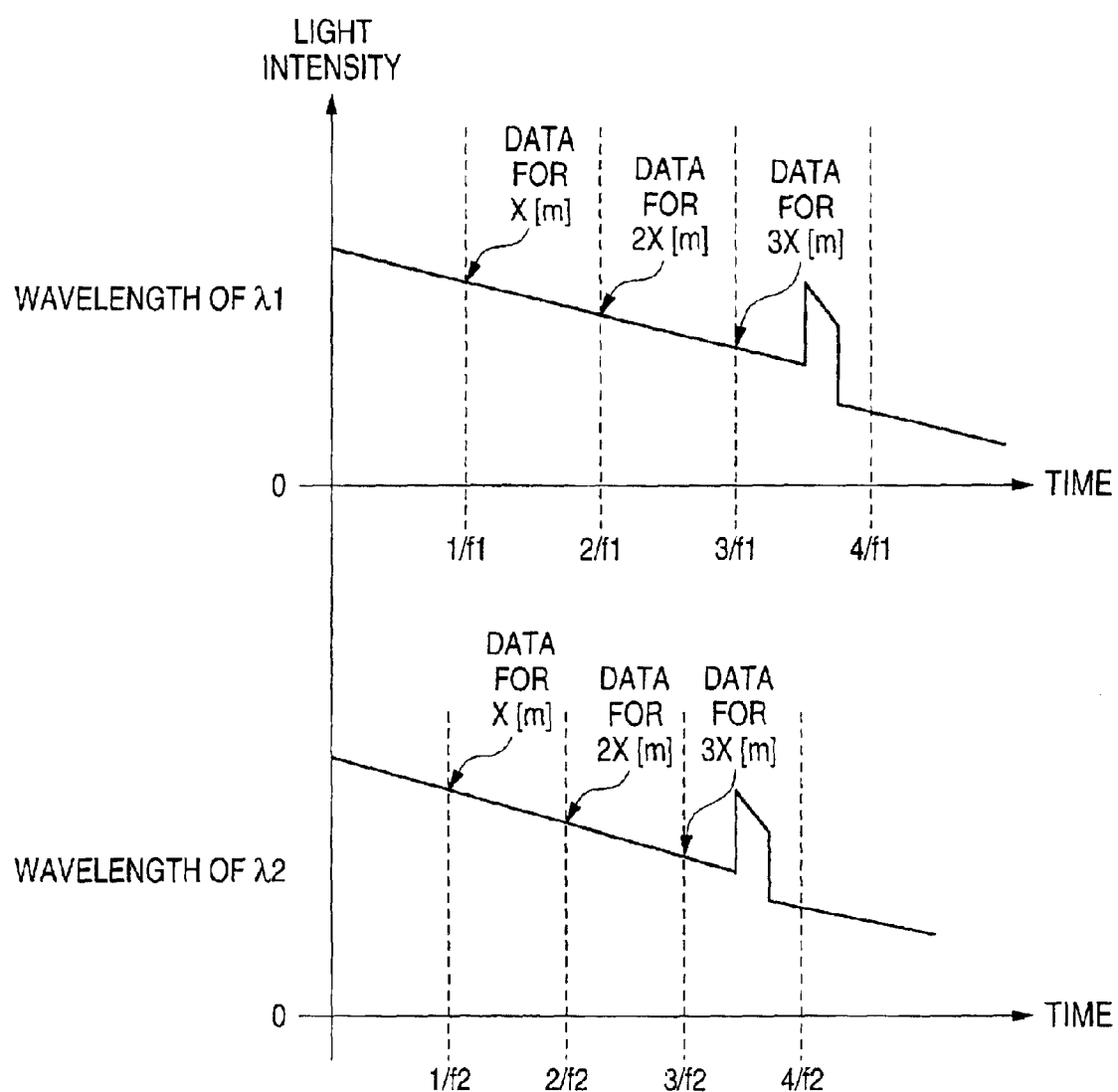
FIG. 2 is a waveform diagram illustrating examples of measurement waveforms of a plurality of different wavelengths obtained in the embodiment shown in FIG. 1.

Next, the data on the generated measurement waveform are respectively subjected to logarithmic conversion in the waveform processing circuit 702 of the display processing section 70, and a rightwardly descending waveform such as the one shown in FIG. 2 is obtained. The data on the measurement waveform subjected to averaging processing and logarithmic conversion are consecutively stored in the storage circuit, and are supplied to the display part 704 to display a desired measurement waveform.

As described above, in accordance with the optical fiber measuring apparatus of this embodiment, when the return light of the plurality of different wavelengths $\lambda 1$ to $\lambda n$ is subjected to signal processing, sampling is effected by sampling clocks each corresponding to the frequency of the respective wavelength, and averaging processing is effected in a case where the phase difference of the sampling clocks falls within a predetermined range, thereby determining a signal waveform based on the return light of the respectively different wavelengths $\lambda 1$ to $\lambda n$. Therefore, the respectively added n-th data can be determined as information for the same distance as the sampling resolution assumes the same value as those of the other wavelengths. Accordingly, at the time when corresponding sampling points in the measurement waveforms are compared, the comparison can be made easily and clearly. In FIG. 2, for example, in the waveforms of the wavelengths $\lambda 1$ and $\lambda 2$, sampling points at each Xm are respectively expressed as being n times the reciprocals of the respective sampling frequencies f1 and f2. As signal levels at their positions are compared, it is possible to measure the state of propagation of the respective wavelengths $\lambda 1$ and $\lambda n$ inside the optical fiber.

Figure 4:
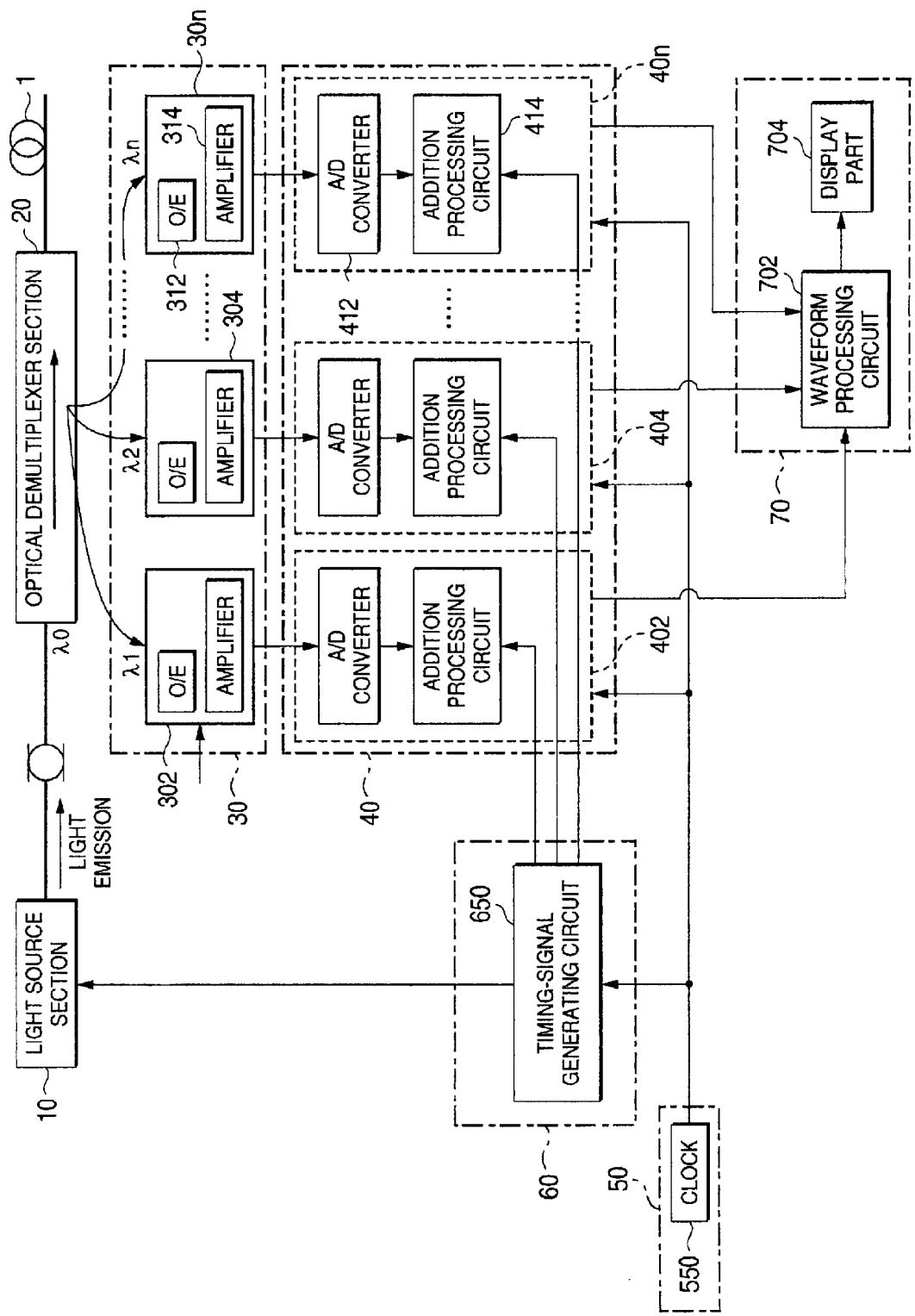
FIG. 4 is a functional block diagram illustrating a comparative example of the optical fiber measuring apparatus.
Figure 5:
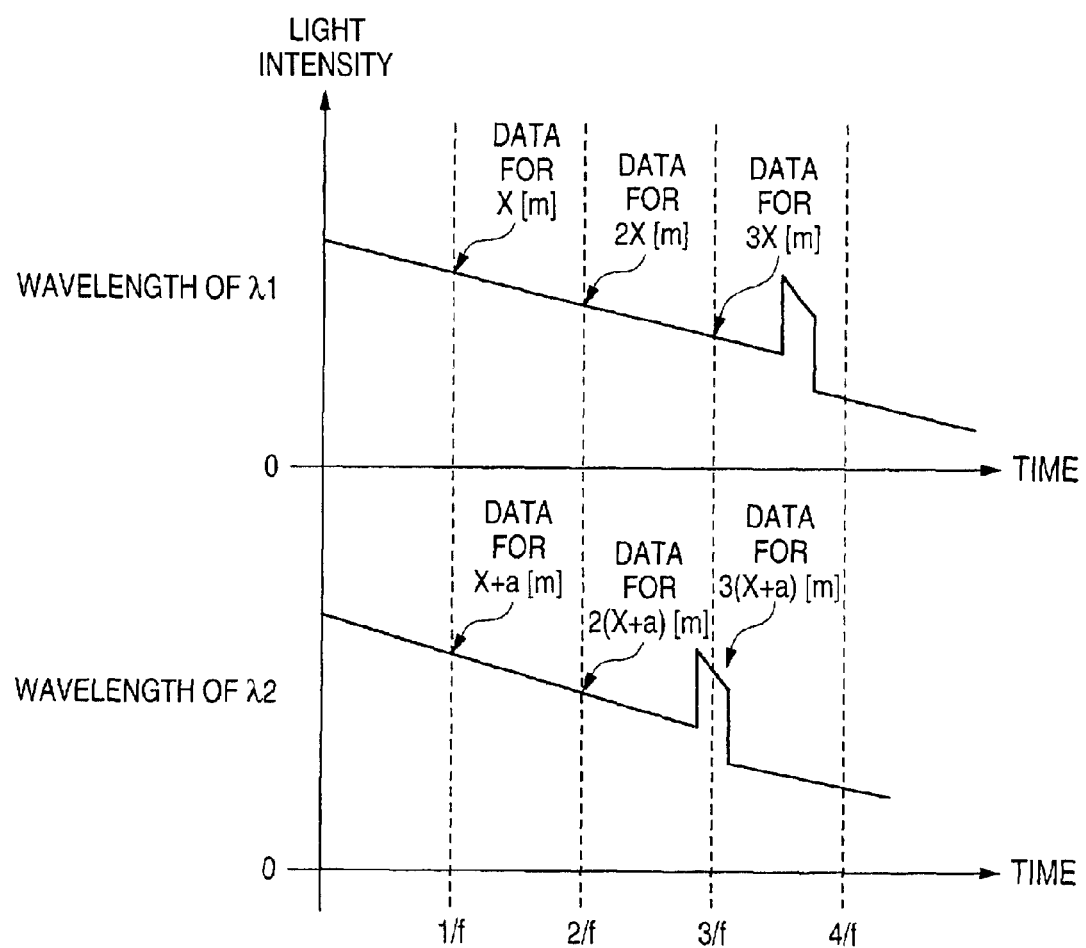
FIG. 5 is a waveform diagram illustrating examples of measurement waveforms of a plurality of different wavelengths obtained in the comparative example shown in FIG. 4.

Furthermore, to clarify the advantages of this embodiment, FIG. 4 shows a comparative example of the optical fiber measuring apparatus, and FIG. 5 shows measurement waveforms of the results. In FIG. 4, the differences with the above-described embodiment lie in that the clock generating section 50 is constituted by a single generator 550, and that a common timing signal is supplied from a timing-signal generating circuit 650 of the timing control section 60 to the addition processing circuits 414 of the signal processing section 40 on the basis of that sampling clock. Consequently, as is apparent from the measurement waveforms shown in FIG. 5, at the respective sampling points each expressed by the reciprocal of the sampling frequency f, the waveform of the wavelength $\lambda 1$ is expressed as being values for each Xm, and the waveform of the wavelength $\lambda 2$ corresponding thereto is expressed as being values for each (X+a)m. For this reason, the longer the distance in the optical fiber, an error occurs for each am, so that it becomes impossible to simply compare signal levels at these sampling points. In this embodiment, the respective sampling points are expressed as values at the same distance in the optical fiber, and they can be compared accurately.

Figure 3:
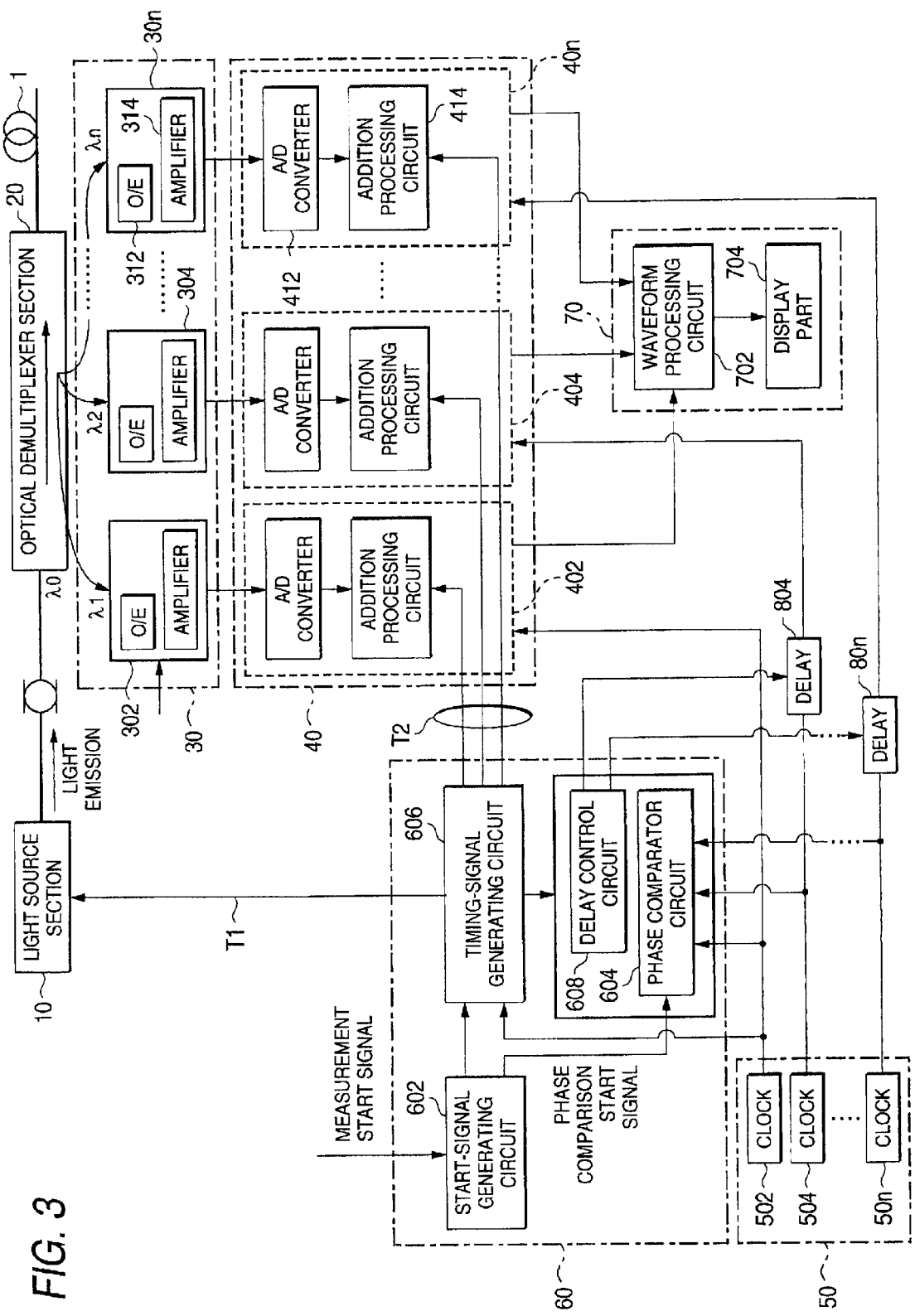
FIG. 3 is a functional block diagram illustrating another embodiment of the optical fiber measuring apparatus in accordance with the invention.

Next, FIG. 3 shows another embodiment of the optical fiber measuring apparatus in accordance with the invention. In this embodiment, differences with the above-described embodiment lie in that sampling clocks from the second to n-th generators 504 to 40n of the clock generating section 50 excluding the first generator 502 are respectively supplied to the processing circuits 404 to 40n of the signal processing section 40 through delay circuits 804 to 80n, and that a delay control circuit 608 for controlling their amounts of delay is provided in the timing control section 60.

Namely, in this embodiment, the timing control section 60 includes the start-signal generating circuit 602, the phase comparator circuit 604, and the timing-signal generating circuit 606 in the same way as the above-described embodiment, and further includes the delay control circuit 608. The start-signal generating circuit 602 in this embodiment detects the pressing of the start button, and supplies a start signal of that result to the timing-signal generating circuit 606 and the phase comparator circuit 604, respectively. The phase comparator circuit 604 compares the phases of the sampling clocks on receiving the start signal from the start-signal generating circuit 602. In a case where the result of that comparison falls within a predetermined range, the phase comparator circuit 604 supplies the result to the delay control circuit 608.

Meanwhile, upon receiving the start signal from the start-signal generating circuit 602, the timing-signal generating circuit 606 supplies the first timing signal T1 to the light source section 10, further generates the second timing signals T2 on the basis of the sampling clock from the first generator 502 of the clock generating section 50, and supplies them to the respective addition processing circuits 414 of the signal processing section 40 and to the delay control circuit 608. The delay control circuit 602 determines the amounts of delay in the delay circuits 804 to 80n on the basis of the result of comparison by the phase comparator circuit 604 and the second timing signal T2 from the timing-signal generating circuit 606, and sets them in the delay circuits 804 to 80n.

As described above, according to the optical fiber measuring apparatus of this embodiment, when the return light of the plurality of different wavelengths $\lambda 1$ to $\lambda n$ is subjected to signal processing, the phase difference of the sampling clocks from the respective generators 502 to 50n of the clock generating section 50, as well as portions of delay until the generation of the second timing signals T2 from the timing-signal generating circuit 606 to the respective addition processing circuits 414 of the signal processing circuit 40, are determined by the delay control circuit 608. The amounts of delay thus determined are set in the respective delay circuits 804 to 80n, thereby making it possible to determine measurement waveforms corresponding to the respective wavelengths of the return light. Hence, it is possible to obtain waveforms similar to those shown in FIG. 2 in the above-described embodiment. Therefore, in the same way as the above-described embodiment, the respectively added n-th data can be determined as information for the same distance as the sampling resolution assumes the same value as those of the other wavelengths. Accordingly, at the time when corresponding sampling points in the measurement waveforms are compared, the comparison can be made easily and clearly.

Although a description is given above of the embodiments of the optical fiber measuring apparatus in accordance with the invention, the optical fiber measuring apparatus in accordance with the invention is not limited to the above-described embodiments, and it goes without saying that changes and modifications within the range that does not depart from the gist of the invention described in the aspects are included in the invention.

As described above, in accordance with the optical fiber measuring apparatus of the invention, there is provided an optical fiber measuring apparatus in which predetermined optical pulses are incident from one end of an optical fiber subject to measurement, and signal levels of return light thereof are detected to measure characteristics of the optical fiber, characterized by comprising: optical-pulse generating section for generating predetermined optical pulses incident upon the optical fiber subject to measurement; optical-pulse input/output section to which the one end of the optical fiber subject to measurement is connected and which makes the optical pulses from the optical-pulse generating section incident upon the optical fiber and detects return light thereof, the optical-pulse input/output section being adapted to demultiplex the return light of the plurality of wavelengths scattered or reflected inside the optical fiber and output the same; a plurality of optical/electrical processing section for converting the light of the respective wavelengths from the optical-pulse input/output section into electrical signals and for amplifying the electrical signals; a plurality of signal processing section for sampling the signals of the respective wavelengths from the optical/electrical processing section and for effecting addition processing with respect to the sampled signals, so as to form waveforms expressing characteristics of the respective wavelengths; a plurality of clock generating section for generating sampling clocks corresponding to speeds of the return light of the respective wavelengths and supplying the sampling clocks to the signal processing section; and timing control section for supplying a first timing signal representing an optical-pulse generating timing to the optical-pulse generating section, and for supplying a second timing signal representing an addition processing timing to each of the signal processing section, the timing control section being adapted to generate the respective timing signals on the basis of a phase difference of the sampling clocks generated by the clock generating section. Accordingly, it is possible to measure the return light of a plurality of different wavelengths in a short time, and its measurement waveforms can be compared accurately.

In accordance with the optical fiber measuring apparatus according to aspect 2, each of the signal processing section includes A/D converting section for effecting analog-to-digital conversion of the signal from the optical/electrical processing section on the basis of the sampling clocks supplied by the clock generating section and for sampling the signal, and addition processing section for effecting addition processing with respect to the signal from the A/D converting section on the basis of the second timing signal from the timing control section, wherein sampling frequencies of the clock generating section are set such that sampling resolutions of the sampling clocks to the A/D converting section assume similar values with respect to the signals of the respective wavelengths, and the timing control section generates the second timing signal to the addition processing section in a case where the phase difference of the sampling clocks from the clock generating section falls within a predetermined range. Accordingly, in measurement waveforms of the return light of the respective wavelengths, which are the results of sampling and addition processing, respective items of data for identical sampling points can be determined as data for an identical distance in the optical fiber, and they can be compared simply and clearly.

In accordance with the optical fiber measuring apparatus according to aspect 3, the timing control section includes phase comparing section for comparing the phases of the sampling clocks generated by the clock generating section, start-signal generating section for generating start signals when the first and the second timing signals are generated on the basis of the result of comparison by the phase comparing section and a measurement start signal at the time of starting measurement, and timing-signal generating section for starting the generation of the first and the second timing signals on the basis of the start signals from the start-signal generating section. Accordingly, as the start button is pressed, the measurement of the plurality of pulses of return light can be executed simply and accurately, and measurement waveforms including data for the identical distance at identical sampling points can be obtained advantageously.

In accordance with the optical fiber measuring apparatus according to aspect 4, each of the signal processing section includes A/D converting section for effecting analog-to-digital conversion of the signal from the optical/electrical processing section on the basis of the sampling clocks supplied by the clock generating section and for sampling the signal, and addition processing section for effecting addition processing with respect to the signal from the A/D converting section on the basis of the second timing signal from the timing control section, wherein the clock generating section supplies the sampling clocks to the A/D converting section with respect to the signals of the respective wavelengths through delay section capable of changing an amount of delay, and the amount of delay of the delay section is calculated on the basis of the phase difference of the sampling clocks generated by the clock generating section. Accordingly, in measurement waveforms of the return light of the respective wavelengths, which are the results of sampling and addition processing, respective items of data for identical sampling points can be determined as data for an identical distance in the optical fiber, and they can be compared simply and clearly.

In accordance with the optical fiber measuring apparatus according to aspect 5, the timing control section includes phase comparing section for comparing the phases of the sampling clocks generated by the clock generating section, start-signal generating section for generating a start signal when the timing signal is generated upon receipt of a measurement start signal at the time of starting measurement, timing-signal generating section for generating the timing signal on the basis of the start signal generated by the start-signal generating section and one of the clocks generated by the clock generating section, and delay control section for controlling the amount of delay of the delay section on the basis of the timing signal from the timing-signal generating section and a result of comparison by the phase comparing section. Accordingly, as the start button is pressed, the measurement of the plurality of pulses of return light can be executed simply and accurately, and measurement waveforms including data for the identical distance at identical sampling points can be obtained advantageously.

What is claimed is:

1. An optical fiber measuring apparatus in which predetermined optical pulses are incident from one end of an optical fiber subject to measurement, and signal levels of return light thereof are detected to measure characteristics of said optical fiber, said optical fiber measuring apparatus comprising:

optical-pulse generating section for generating predetermined optical pulses incident upon said optical fiber subject to measurement;

optical-pulse input/output section to which the one end of said optical fiber subject to measurement is connected and which makes the optical pulses from said optical-pulse generating section incident upon said optical fiber and detects return light thereof, said optical-pulse input/output section being adapted to demultiplex the return light of the plurality of wavelengths scattered or reflected inside said optical fiber and output the same;

a plurality of optical/electrical processing section for converting the light of the respective wavelengths from said optical-pulse input/output section into electrical signals and for amplifying the electrical signals;

a plurality of signal processing section for sampling the signals of the respective wavelengths from said optical/electrical processing section and for effecting addition processing with respect to the sampled signals, so as to form waveforms expressing characteristics of the respective wavelengths;

a plurality of clock generating section for generating sampling clocks corresponding to speeds of the return light of the respective wavelengths and supplying the sampling clocks to said signal processing section; and timing control section for supplying a first timing signal representing an optical-pulse generating timing to said optical-pulse generating section, and for supplying a second timing signal representing an addition processing timing to each of said signal processing section, said timing control section being adapted to generate the respective timing signals on the basis of a phase difference of the sampling clocks generated by said clock generating section.

2. The optical fiber measuring apparatus according to claim 1, wherein each of said signal processing section includes A/D converting section for effecting analog-to-digital conversion of the signal from said optical/electrical processing section on the basis of the sampling clocks supplied by said clock generating section and for sampling the signal, and addition processing section for effecting addition processing with respect to the signal from said A/D converting section on the basis of the second timing signal from said timing control section, sampling frequencies of said clock generating section are set such that sampling resolutions of the sampling clocks to said A/D converting section assume similar values with respect to the signals of the respective wavelengths, and said timing control section generates the second timing signal to said addition processing section in a case where the phase difference of the sampling clocks from said clock generating section falls within a predetermined range.

3. The optical fiber measuring apparatus according to claim 2, wherein said timing control section includes phase comparing section for comparing the phases of the sampling clocks generated by said clock generating section, start-signal generating section for generating start signals when the first and the second timing signals are generated on the basis of the result of comparison by said phase comparing section and a measurement start signal at the time of starting measurement, and timing-signal generating section for starting the generation of the first and the second timing signals on the basis of the start signals from said start-signal generating section.

4. The optical fiber measuring apparatus according to claim 1, wherein each of said signal processing section includes A/D converting section for effecting analog-to-digital conversion of the signal from said optical/electrical processing section on the basis of the sampling clocks supplied by said clock generating section and for sampling the signal, and addition processing section for effecting addition processing with respect to the signal from said A/D converting section on the basis of the second timing signal from said timing control section, said clock generating section supplies the sampling clocks to said A/D converting section with respect to the signals of the respective wavelengths through delay section capable of changing an amount of delay, and the amount of delay of said delay section is calculated on the basis of the phase difference of the sampling clocks generated by said clock generating section.

5. The optical fiber measuring apparatus according to claim 4, wherein said timing control section includes phase comparing section for comparing the phases of the sampling clocks generated by said clock generating section, start-signal generating section for generating a start signal when the timing signal is generated upon receipt of a measurement start signal at the time of starting measurement, timing-signal generating section for generating the timing signal on the basis of the start signal generated by said start-signal generating section and one of the clocks generated by said clock generating section, and delay control section for controlling the amount of delay of said delay section on the basis of the timing signal from said timing-signal generating section and a result of comparison by said phase comparing section.

* * * * *